(12) United States Patent
Stirnemann

(10) Patent No.: US 9,271,666 B2
(45) Date of Patent: Mar. 1, 2016

(54) METHOD OF PROCESSING A SIGNAL IN A HEARING INSTRUMENT, AND HEARING INSTRUMENT

(75) Inventor: Alfred Stirnemann, Zollikon (CH)

(73) Assignee: SONOVA AG, Staefa (CH)

( * ) Notice: Subject to any disclaimer, the term of this patent is extended or adjusted under 35 U.S.C. 154(b) by 99 days.

(21) Appl. No.: 14/359,139

(22) PCT Filed: Nov. 22, 2011

(86) PCT No.: PCT/CH2011/000277
§ 371 (c)(1),
(2), (4) Date: May 30, 2014

(87) PCT Pub. No.: WO2013/075255
PCT Pub. Date: May 30, 2013

(65) Prior Publication Data
US 2014/0321657 A1    Oct. 30, 2014

(51) Int. Cl.
*H04R 29/00* (2006.01)
*A61B 5/12* (2006.01)
*H04R 25/00* (2006.01)
*A61B 5/00* (2006.01)

(52) U.S. Cl.
CPC ............... *A61B 5/125* (2013.01); *A61B 5/6817* (2013.01); *H04R 25/606* (2013.01); *H04R 25/70* (2013.01); *H04R 2225/021* (2013.01); *H04R 2225/023* (2013.01); *H04R 2225/025* (2013.01)

(58) Field of Classification Search
CPC .................. H04R 25/70; H04R 25/606; H04R 2225/021; H04R 2225/025; H04R 2225/023; A61B 5/125; A61B 5/6817
USPC ............................ 381/60, 312, 328, 23.1, 58
See application file for complete search history.

(56) References Cited

U.S. PATENT DOCUMENTS

2007/0036377 A1* 2/2007 Stirnemann .......... H04R 25/505
381/315

FOREIGN PATENT DOCUMENTS

| EP | 1594344 | 11/2005 |
|---|---|---|
| EP | 1830602 | 9/2007 |

OTHER PUBLICATIONS

Munro, Kevin Jr., et al.; "Measuring the Real-Ear to Coupler Difference Transfer Function with an Insert Earphone and a Hearing Instrument: Are They the Same?", Ear and Hearing, vol. 26, No. 1, Feb. 1, 2005.

* cited by examiner

*Primary Examiner* — Paul S Kim
(74) *Attorney, Agent, or Firm* — Rankin, Hill & Clark LLP

(57) ABSTRACT

A method of estimating an acoustic transfer quantity representative of a sound pressure transfer to the eardrum includes the steps of measuring, by an ear canal microphone of the hearing instrument, an acoustic signal in the ear canal when a sound signal is emitted into the ear canal by a receiver of the hearing instrument, the ear canal microphone being in acoustic communication with the ear canal, determining, from the acoustic signal and from a frequency dependent reference characteristics of the hearing instrument, an ear canal impedance, and, calculating, from the ear canal impedance, an estimate of the acoustic transfer quantity.

13 Claims, 8 Drawing Sheets

$$\begin{bmatrix} \text{RECD} \end{bmatrix} = \begin{bmatrix} M \end{bmatrix} \begin{bmatrix} Z_{ec} \end{bmatrix}$$

METHOD OF PROCESSING A SIGNAL IN A HEARING INSTRUMENT, AND HEARING INSTRUMENT

BACKGROUND OF THE INVENTION

1. Field of the Invention

The invention relates to a method of processing a signal in a hearing instrument, and to a hearing instrument, in particular a hearing aid.

2. Description of Related Art

The acoustic coupling of hearing instruments to the tympanic membrane (TM/eardrum) is usually described by means of the Real-Ear-to-Coupler-Difference (RECD) that is indicative of the difference between the sound pressure at the 2 cc coupler (a standardized artificial model of the ear canal) and the sound pressure at the eardrum.

Another quantity that describes the acoustic interplay between the hearing instrument (or that part of the hearing instrument (earpiece) that is inserted into the ear) and the real ear is the Real Ear Occluded Gain (REOG). The REOG describes the sound pressure signal transfer for a sound signal incident on the ear to the eardrum when the hearing instrument is turned off.

According to prior art methods, taking into account the individual situation in a real person's ear canal requires, for example, the measurement by a microphone probe in front of the eardrum. Such a measurement is not straightforward, is time consuming and requires special equipment. Also, the protruding probe end is prone to being soiled and may cause displeasing sensations to the patient. Further, the measurement is of limited accurateness because due to the introduction of the probe, additional leakage may be caused through the earpiece. Also, the equipment would need to be calibrated to equate sensitivity variations. In addition, there are individual differences because of tubings of different lengths and variations of the earwax protection. Correction methods either require a SPICE-model fit or data stored in look-up tables. Further, estimations of the corrections are not compatible with the common Real-Ear-to-Coupler Difference (RECD).

Examples of methods to estimate the sound pressure at the eardrum by a probe that is placed not at the eardrum, but away from it are, for example, disclosed in US 2010/0202642 and in WO 2010/016925. In WO 2010/016925, the distance between the probe microphone and the eardrum is estimated based on the $\lambda/4$ resonance. The $\lambda/4$ resonance is a pronounced dip in the sound level in the ear canal. This is then used to correct the estimated sound pressure level at the TM by adding the 'inverse of the dip function'. While these methods provide some improvement over the prior art in terms of avoiding direct probe contact to the eardrum, they still require a separate probe.

Many future hearing instruments will have an ear canal microphone for active occlusion control. Active occlusion control measures the sound level in the ear canal—by the ear canal microphone—and submits the inverse of the measured signal (filtered by a specific function) to the receiver input. US 2006/0083395 proposes to measure, by means of an ear canal microphone, the acoustic reflectance (the ratio of the reflected pressure that comes from eardrum and cochlea and of the incident pressure) for automatically adjusting processing parameters of a hearing aid. In the reflectance measurements, a measured impedance may be used as an input parameter.

However, an estimation of the sound pressure at the eardrum—and thus also of the RECD—by means of the acoustic reflection or another power quantity is not possible without further input data, especially an estimate of the ear canal cross section.

Most ear canal microphone applications are restricted to controlling the microphone sound pressure and neither comprise calibration nor an estimation of the eardrum sound pressure. Current models therefore do not appropriately consider the transfer from the ear canal microphone to the eardrum.

BRIEF SUMMARY OF THE INVENTION

It is an object of the invention to provide method of determining the acoustic coupling of a hearing instrument to the eardrum or another real ear acoustic quantity that overcomes disadvantages of prior art approaches and that especially does not require a probe separate from the hearing instrument to be introduced into the ear canal.

A concept of the invention is to use a hearing instrument specific acoustic ear canal impedance characteristic for estimating a sound pressure level at the eardrum without the use of any probe medial of an earpiece (i.e. closer to earpiece).

In the present text, 'earpiece' generally refers to an ITE/ITC/CIC hearing instrument, or that part of a hearing instrument with components outside of the ear (such as a BTE hearing instrument) which is placed in the ear. In other words, while in some hearing instruments, the hearing instrument consists of the earpiece, in other hearing instruments the earpiece is one part of the hearing instrument and is in communication with another part of the hearing instrument, for example, a behind-the-ear component.

The earpiece in many embodiments comprises a hard or possibly soft shell with a shape adapted to the shape of the individual's ear canal. In some embodiments, it may alternatively be of a 'universal fit' type that comprises a soft tip that adapts to the ear canal. The shell may comprise active components, such as the microphones and the receiver as well as the signal processor and a battery for ITE/ITC/CIC hearing instruments, or at least a receiver for some of the BTE hearing instruments, or it may merely be configured to hold a tubing that connects the other component(s) to the ear.

Often, the earpiece will comprise a so-called vent, i.e. a small channel connecting the closed-off remaining volume in front of the eardrum with the outside.

In accordance with a first aspect of the invention, a method of estimating an acoustic transfer quantity representative of a sound pressure transfer to the eardrum is provided, the method comprising the steps of measuring, by an ear canal microphone of the hearing instrument, an acoustic signal in the ear canal when a sound signal is emitted into the ear canal by a receiver of the hearing instrument, the ear canal microphone being in acoustic communication with the ear canal;

determining, from the acoustic signal and from a frequency dependent reference characteristics of the hearing instrument, an ear canal impedance; and calculating, from the ear canal impedance, an estimate of the acoustic transfer quantity.

In this, the ear canal microphone, like the receiver, is in direct (acoustic) communication with the ear canal volume that remains between the earpiece and the eardrum. 'Direct communication' in this context implies that an input or output, respectively, of the microphone/the receiver either opens into the volume or is connected by a dedicated sound conductor, such as a tubing, with the volume. A mere inevitable coupling via the shell, the human tissue and/or the vent is not considered a direct acoustic coupling.

The hearing instrument reference characteristic will preferably be ear independent. It may be characteristic of an acoustic quantity of the hearing instrument coupled to a standard acoustic coupler.

The impedance determined based on the measurement of the acoustic signal by the ear canal microphone depends on the ear canal microphone and possibly on influences of individual receiver an microphone sensitivities and tubings etc. Taking into account the frequency dependent characteristics may deal with this kind of dependence. The frequency dependent characteristics may, for example, be a frequency dependent microphone signal (sound pressure signal) measured by the ear canal microphone when the hearing instrument's earpiece is coupled to such a standard acoustic coupler, such as a 2 cc coupler. This characteristics may either be measured individually for the hearing instrument and thereafter stored in its memory, for example, by the manufacturer prior to delivery of the hearing instrument. Alternatively, standard values representing an average of the values for a certain hearing instrument model can be stored in the memory. Then, all hearing instruments of a certain model have identical characteristics. The sound signals used for the measurement with the ear canal microphone and the receiver coupled to the ear canal and for the measurement with the ear canal microphone and the receiver coupled to the standard acoustic coupler may be the same. For example, sound signals with a broad, possibly flat frequency distribution or sound signals that vary as a function of time may be used.

Possibilities to determine the reference characteristics of the hearing instrument may be classified as follows:

using a general internal reference (for example, representing an average of the values for a certain hearing instrument model);

using a (for example, custom manufactured) calibration volume and the hearing instrument ear canal microphone;

using several (for example, custom manufactured) calibration elements and the hearing instrument ear canal microphone; and using one or more calibration volumes with a calibration microphone.

The ear canal impedance may be an impedance for sound emitted in a sound entrance plane in the ear canal, the sound entrance plane being, for example, the inner (medial) end plane of the hearing instrument's earpiece. The impedance is thus, for example, the ratio of the sound pressure level in the sound entrance plane and of the sound flow in the same plane. The sound entrance plane may be the plane in which the tubing from the receiver opens into the ear canal. This plane may correspond to the plane in which the tubing from the ear canal microphone opens into the ear canal.

In accordance with a possibility, in the step of measuring the ear canal impedance, the ear canal impedance is measured by means of a test signal emitted by the receiver and measured by the ear canal microphone. In other embodiments, the 'normal' wanted acoustic signal emitted by the receiver is used to measure the impedance. By using the acoustic quantity of the hearing instrument coupled to the standard acoustic coupler this effect can be compensated when calculating the ear canal impedance from the measured signal.

It is an insight underlying embodiments of the present invention that a simplified impedance measurement that takes into account reference data of the hearing instrument, for example, coupled to a standard coupler, and a simple measurement of the sound pressure by an ear canal microphone can be used to measure the impedance in the ear. The fact that data gained on a single standard coupler can be used as an expedient input for determining the impedance of a real ear canal is surprising. One reason for this is that it has been found that in a hearing instrument, the receiver can be approximated to be an ideal sound flow source, so that the sound flow produced by the receiver becomes approximately independent on the acoustic impedance that it is coupled to. Only due to this insight it becomes possible to use sound signal data recorded from measurements on a single standard volume for determining the real ear canal impedance.

It is a further insight underlying embodiments of the present invention that the ear canal impedance—more in particular impedance at a sound entrance plane—is a good input quantity for calculating a sound pressure transfer quantity such as the Real-Ear-to-Coupler-Difference (RECD).

According to a possibility, prior to the step of calculating an estimate of the acoustic transfer quantity from the acoustic impedance, at least one of the following steps is carried out:

estimating a physical property of the ear canal; and estimating a leak impedance of sound leaking through a hearing instrument vent and/or through a leaky shell.

In case step a. is carried out, in the step of calculating the estimate of the acoustic transfer quantity, said acoustic quantity is calculated from the acoustic impedance and from the estimated geometrical parameter. In case step b. is carried out, in the step of calculating the acoustic quantity indicative of the sound pressure at the eardrum, the acoustic quantity is calculated from the acoustic impedance (ear canal impedance) and the estimated leak impedance.

Whereas some embodiments rely on the combination of steps a. and b., in many embodiments of the invention, exactly (only) one of steps a. and step b. is carried out.

The quantity indicative of the acoustic transfer may be the transfer impedance $Z_{trans}=p_{dr}/q_{ec}$ (dr=eardrum ec=ear canal). Alternatively, it may be the closely related RECD or another acoustic coupling quantity.

It is a further insight underlying embodiments of the present invention that the transfer impedance is a deciding quantity because hearing instrument receivers have been found to be almost ideal sound flow sources, i.e. the source impedance is so high that it can be neglected. In other words, hearing aid receivers are rather sound flow sources than sound pressure sources, whereas at the eardrum the sound pressure is of interest. The ultimately interesting quantity is the transfer impedance $Z_{trans}=p_{dr}/q_{ec}$.

It is yet another insight that the acoustic behavior of the ear canal can be described to be a two-port network because of the load dependence it exhibits. Applying Thévenin's theorem, hearing aid and ear canal can be modeled by an ideal sound source with a source impedance and a two-port loaded by the ear drum impedance.

In an example, the acoustic quantity is a transfer quantity indicative of the acoustic transfer from the receiver to the eardrum, for example, the Real-Ear-to-Coupler difference (RECD) or the sound pressure transfer function. It is an insight underlying embodiments of the present invention that for an acoustic quantity that is indicative of the transfer from the receiver to the sound pressure at the eardrum (such as the RECD), very good estimates are possible based on the ear canal impedance and physical properties of the ear canal only. The dependence on other quantities, such as the leak impedance, and the influence of anatomical quantities such as the characteristics of the eardrum, characteristics of the surrounding tissue, bone structure, mechanical coupling of the earpiece to the ear canal etc. can be neglected and/or are adequately taken into account in the ear canal impedance.

In examples, the physical property of the ear canal is a geometrical property. For example, the physical property may be the length of the remaining volume between the earpiece and the eardrum—i.e. the distance between the earpiece and the eardrum. This distance may, for example, be estimated based on the quarter wavelength resonance known from the prior art. The frequency dependence of a signal measured by the ear canal microphone is analysed. A frequency at which the signal is at a local extreme—especially a local minimum—is identified. The distance is then calculated to be a quarter of the wavelength corresponding to the identified frequency.

In another example, the influence of the physical property is taken into account by an anatomically inspired model in which the outer ear and the middle ear are modeled by a network of impedances or at least one piece of tubing and impedances, the values for the impedances/tubing then being fitted to bring the frequency dependent acoustic input impedance of the model into the best correspondence with the according measured values.

In yet another example the influence of the physical property is taken into account by a statistical linear or nonlinear model.

It is yet another insight underlying embodiments of the present invention, that for an acoustic quantity that is indicative of the transfer from outside of the ear to the sound pressure at the eardrum (especially the Real Ear Occluded Gain (REOG)), it is possible to make good estimates based on the ear canal impedance and the leak impedance. The combination of estimates of the leak impedance and of a physical property of the ear canal can lead to even further improved estimates. The REOG is the sound pressure level at the eardrum in relation to the sound pressure level of incident ambient sound when the hearing instrument is turned off, as a function of the frequency.

In an example, the REOG is estimated from the ear canal impedance and from the leak impedance (only).

In another example, the REOG is estimated from the ear canal impedance, from the leak impedance and in addition from a geometrical quantity of the ear canal, for example, the length of the remaining volume determined from the hereinbefore mentioned dip at a quarter of the wavelength.

In accordance with a second aspect of the invention, a method of estimating an acoustic transfer quantity representative of a sound pressure transfer to the eardrum is provided, the method comprising the steps of:

measuring, by an ear canal microphone of the hearing instrument, an acoustic signal in the ear canal acoustic when a sound signal is emitted into the ear canal by a receiver of the hearing instrument, the ear canal microphone being in acoustic communication with the ear canal;

estimating a physical property of the ear canal and/or a leak impedance of sound leaking through a hearing instrument vent and/or through a leaky earpiece shell; and calculating, from the results of measuring the acoustic signal and of estimating the physical property and/or leak impedance, an estimate of the acoustic transfer quantity.

In the step of calculating the acoustic transfer quantity, influences of properties of the hearing instrument may be taken into account by means of stored values representing characteristics of the hearing instrument itself. Especially, the stored values may represent a frequency dependent characteristics of an acoustic quantity of the hearing instrument when it is coupled to a standard acoustic coupler, such as a 2 cc coupler or a smaller or possibly larger coupler. The hereinbefore and hereinafter taught characteristics and possible method steps that relate to determining these stored values also are pertinent for the second aspect of the invention. The same holds for the step of estimating a physical property of the ear canal and/or a leak impedance of sound leaking through a hearing instrument vent and/or through a leaky earpiece shell.

In all aspects and embodiments that deal with estimating an acoustic quantity representative of a sound pressure at the eardrum, a step of adjusting a hearing instrument processing parameter may follow, which adjustment is based on the result of the estimate of the acoustic quantity. For example, if the acoustic quantity is the RECD, the adjustment may be a correction, by a function corresponding to the RECD, of the calculated frequency dependent gain that is applied to the incident signal.

Determining an ear canal impedance and/or an acoustic transfer quantity representative of the sound pressure transfer to the eardrum by means of an ear canal microphone that measures a signal generated by a hearing instrument receiver may be viewed as a simplified impedance measurement. The measured values will generally depend on properties of the hearing instrument itself, especially receiver, tubing and possibly the ear canal microphone. According to a third aspect of the present invention, the hereinbefore discussed frequency dependent characteristics of an acoustic quantity of the hearing instrument coupled to a standard acoustic coupler or any other hearing instrument characteristics may be measured by means of a customized standard acoustic coupler.

According to the third aspect of the invention, therefore, a standard acoustic coupler is provided, the standard acoustic coupler comprising an interior space with a defined volume and with an opening, the opening being custom shaped to fit to the earpiece of a hearing instrument.

A method of measuring a hearing instrument characteristics comprises providing the hearing instrument with a custom shaped earpiece adapted to the shape of an ear canal of a hearing instrument wearer, of custom manufacturing a standard acoustic coupler comprising an interior space with a defined volume and with an opening that is shaped to be adapted to the shape of the hearing instrument, of coupling a sound signal into the interior space and of measuring the resulting frequency dependent acoustic signal in the interior space. In this, the sound signal is produced by the hearing instrument receiver (that then is, through the opening, in direct acoustic communication with the interior space) and/or the acoustic signal is measured by a hearing instrument's ear canal microphone (that then is, through the opening, in direct acoustic communication with the interior space).

The custom manufacturing of the calibration element (the standard acoustic coupler) may be done using data directly obtained from molding the ear canal and/or from measurement performed at the ear canal. In addition or as an alternative, data obtained from performing measurements at the earpiece itself may be used.

The standard acoustic coupler in this serves as a calibration element. It may have a size of 2 cm$^3$ (volume of interior space) or a size different therefrom (for example, smaller)

In accordance with an alternative, the measurement is done by a separate measurement microphone provided within the test volume of the calibration element. Then, in addition to the acoustic impedance reference, the individual Output sensitivity (SensOut) value may be determined at the same time.

BRIEF DESCRIPTION OF THE DRAWINGS

Hereinafter, embodiments of methods and devices according to the present invention are described in more detail referring to the figures. In the drawings, same reference numerals refer to same or analogous elements. The drawings are all schematical.

DETAILED DESCRIPTION OF THE INVENTION

Figure 1:
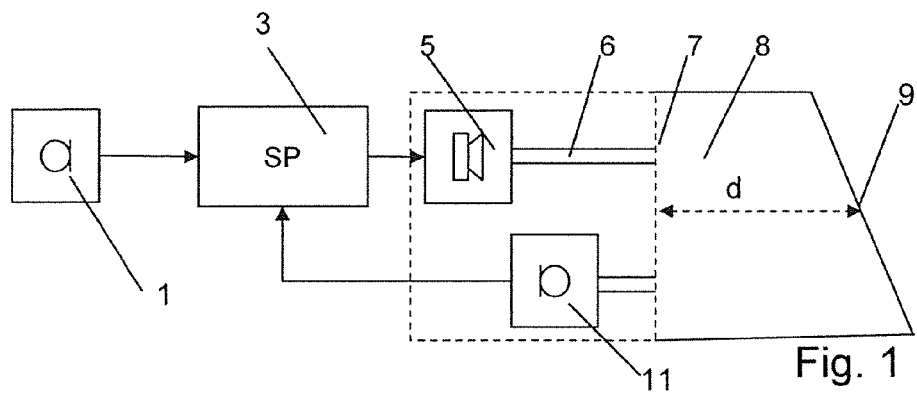
FIG. 1 is a simplified schematic of a hearing instrument with an earpiece inserted in an ear so that a remaining volume between the earpiece and the eardrum is defined.

The hearing instrument schematically represented in FIG. 1 may be of the behind-the-ear (BTE) type, of the in-the-ear (ITE) type, (of the completely-in-the-canal (CIC) type or not) or of any other type. It comprises an input microphone 1. In practice, often more than one input microphones are used, and/or in addition to the input microphone further receiving means for receiving signals may be present, such as a telecoil receiver, a receiving unit including an antenna for receiving wirelessly transmitted signals, etc. The electrical input signal obtained from the at least one input microphone is processed by a signal processing unit 3 to obtain an electrical output signal. The signal processing unit 3 depicted in FIG. 1 may comprise analog-to-digital conversion means and any other auxiliary means in addition to a digital signal processing stage. The signal processing unit may be physically integrated in a single element or may comprise different elements that may optionally be arranged at different places, including the possibility of having elements placed in an earpiece and other parts at another place, for example, in a behind-the-ear unit.

The electrical output signal is converted into an acoustic output signal by at least one receiver (loudspeaker) 5 and is emitted into a remaining volume 8 between the user's eardrum 9 and the in-the-ear-canal-component of the hearing instrument. The hearing instrument further comprises an ear canal microphone 11 operable to convert an acoustic signal in the ear canal into an electrical signal supplied to the signal processing unit 3. The sound entrance plane 7 that terminates the remaining volume corresponds to the plane that is defined by the locations where the sound openings between the receiver/ear canal microphone and the remaining volume 8 are located. In most cases, the sound entrance plane 7 is the inner end plane of the hearing instrument's earpiece.

Generally, also pertaining to other principles and embodiments of the invention discussed herein, the ear canal microphone is part of the hearing instrument and present in the earpiece of the hearing instrument or possibly outside of the earpiece and connected to the earpiece by a tubing that opens out into the remaining volume 8. Especially, the ear canal microphone does not require—or form part of—any separate probe that goes further into the ear canal than the earpiece itself.

Figure 2A:
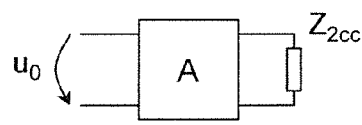
FIGS. 2a and 2b are a matrix model and a Thévenin model of the acoustic transfer to the 2 cc coupler.
Figure 3A:
FIGS. 3a and 3b are a matrix model and a Thévenin model of the acoustic transfer to the real ear drum.
Figure 2B:
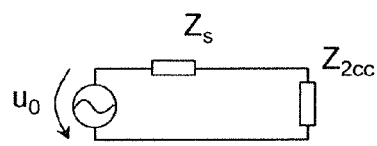
Figure 3B:
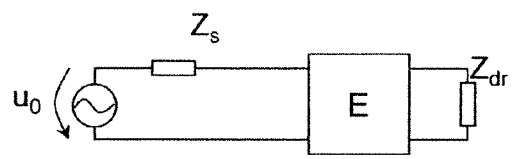

FIGS. 2a and 2b show the transmission system for the coupling of the hearing instrument to a 2 cc coupler, and FIGS. 3a and 3b show the coupling to the real ear. Matrix A describes the transmission behavior of the receiver and the tubing, whereas matrix E (that acts on the vector comprising the sound pressure and the sound flow as coefficients) describes the transmission path from the sound entrance plane to the eardrum and, if applicable, also the influence of the vent, leakage etc.

Assuming that the receiver and the tubing of both systems are identical, Thévenin' theorem holds that the behavior of the receiver and tubing in both cases can be described by a replacement voltage source and a source impedance $Z_s$. The RECD can then be obtained from the following expression:

$$RECD = \frac{Z_{dr}}{Z_{2cc}} \cdot \frac{Z_s + Z_{2cc}}{Z_s(e_{21}Z_{dr} + e_{22}) + (e_{11}Z_{dr} + e_{12})}$$

Whereas in some models, the impedance $Z_{dr}$ of the eardrum is estimated to be infinity, in reality, it has been found to amount to about three times the impedance of the ear canal.

The source impedance $Z_s$ may be calculated from the matrix coefficients $a_{11}$ and $a_{12}$ of Matrix A and therefore corresponds to the output-side impedance $Z_{out}$ of matrix A when the input side is shorted.

$$Z_s = \frac{a_{12}}{a_{11}}$$

Figure 4A:
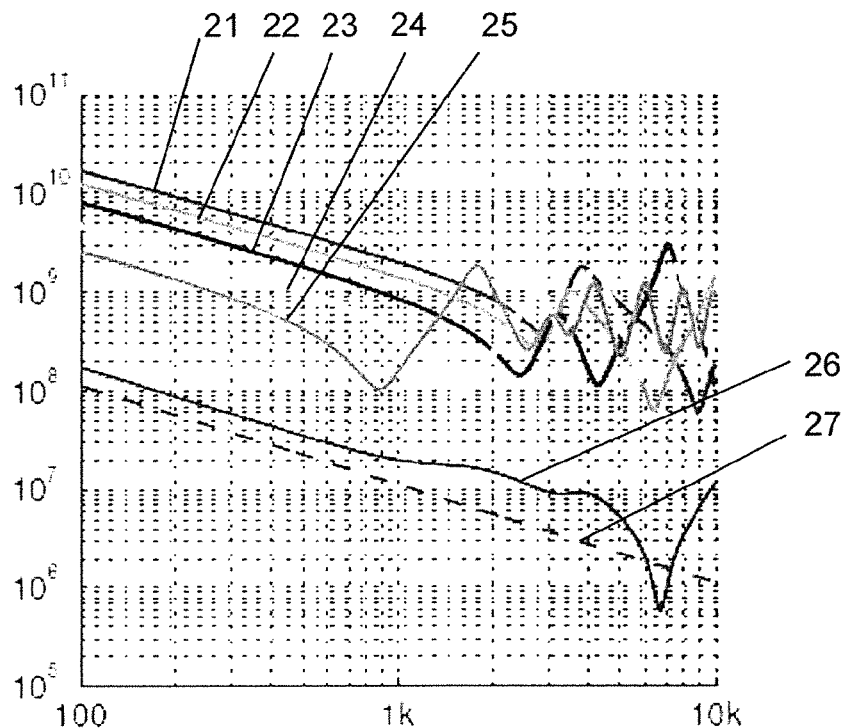
FIGS. 4a and 4b are graphs illustrating simulations of the source impedance of a Knowles FK200 receiver for different tubings.
Figure 4B:
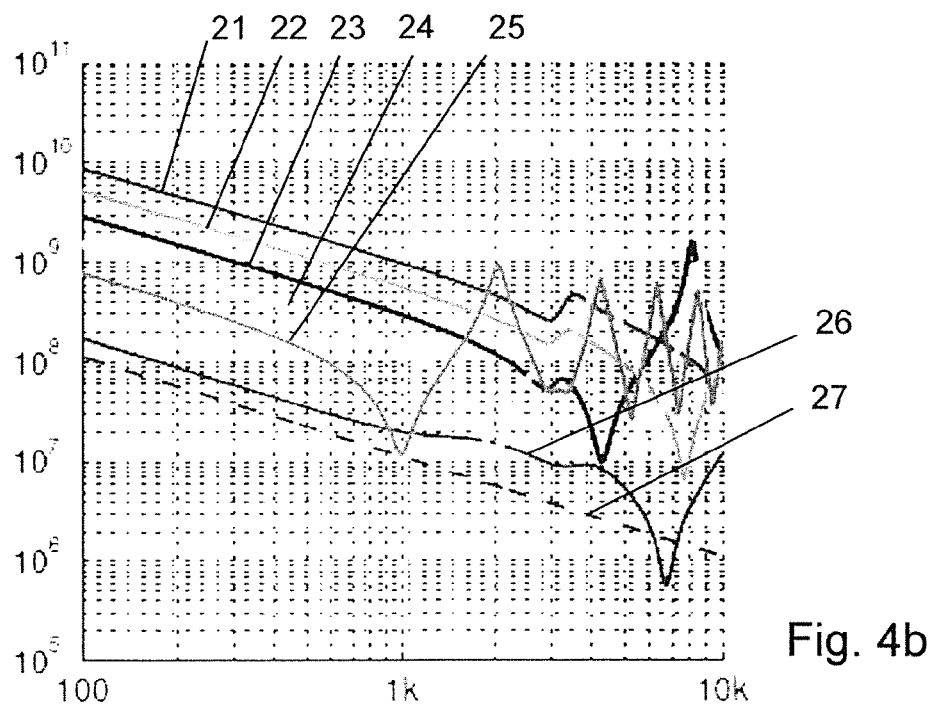

FIGS. 4a and 4b show the values of simulated source impedances $Z_s$ of a Knowles FK200 receiver in combination with two different tubing diameters and five different tubing lengths. In FIG. 4a, the acoustic impedance (in $Ns/m^5$) is shown as a function of the frequency in Hz (1 k=1 kHz) for a 1 mm tubing diameter and of 5 mm (21), 10 mm (22), 20 mm (23), 40 mm (24), and 80 mm (25) length. In addition, for comparison, the input impedance of the ear simulator 26 and the impedance of the 2 cc coupler 27 are illustrated. FIG. 4b shows the corresponding values for a 2 mm tubing diameter, again for 5 mm (21), 10 mm (22), 20 mm (23), 40 mm (24), and 80 mm (25) length, and in comparison the input impedance of the ear simulator 26 and the impedance of the 2 cc coupler 27.

One can see that the source impedances are the smaller the longer and broader the tubing. For a diameter of 1 mm, all source impedances are clearly above the input impedance of the ear simulator. Even at the position of the minimum of the smallest source impedance, the latter is still almost a decade above the impedance of the ear simulator. In relation to the typical input impedance of the ear and to the impedance of the 2 cc volume, the source impedance is, at least for the 1 mm tubing, very large. This justifies the assumption that the receiver and tubing approximately constitute an ideal sound flow source that has a source impedance of $Z_s=\infty$, thus of a constant sound flow $q_0$ in the sound entrance plane of the ear canal. As a consequence, the calculation of the RECD simplifies to the following expression:

$$RECD = \frac{Z_{dr}}{Z_{2cc}} \cdot \frac{1}{e_{21}Z_{dr} + e_{22}} = \frac{Z_{trans}}{Z_{2cc}}$$

The transfer impedance $Z_{trans}$ corresponds to the sound pressure $p_{dr}$ at the eardrum in relation to the sound flow $q_o$ in the sound entrance plane of the coupling to the ear. It can be calculated both, in dependence of the eardrum impedance $Z_{dr}$ (see above), and in dependence of the ear canal impedance $Z_{ec}$ (the ratio of the sound pressure in the entrance plane and the sound flow in the entrance plane):

$$Z_{trans} = \frac{Z_{dr}}{e_{21}Z_{dr} + e_{22}} = e_{22}Z_{ec} - e_{12}$$

(In these considerations, the sound leakage, for example, produced by the vent is neglected; see also the description of FIG. 13a hereinafter). For the ear canal impedance $Z_{ec}$ and the impedance of the 2 cc coupler the following holds:

$$Z_{ec} = \frac{p_{ec}}{q_0}; Z_{2cc} = \frac{p_{2cc}}{q_0}$$

Under the assumption made that the sound source is an ideal sound flow source with the constant sound flow $q_0$, the ratio of both impedances corresponds to the ratio of the sound pressures $p_{ec}$ and $p_{2\,cc}$. If the—known—impedance of the 2 cc volume is used, this yields the ear canal impedance $Z_{ec}$ as a function of the ratio of the sound pressures:

$$Z_{ec} = Z_{2cc} \cdot \frac{p_{ec}}{p_{2cc}}$$

In contrast to general impedance measurement processes, this method just requires a single calibration measurement. However, it relies on an—approximately—ideal sound flow source and a microphone position in the measurement plane. For the RECD, the following expression is obtained:

$$RECD = \frac{Z_{trans}}{Z_{2cc}} = \frac{e_{22}Z_{ec} - e_{12}}{Z_{2cc}} = e_{22}\frac{p_{ec}}{p_{2cc}} - \frac{e_{12}}{Z_{2cc}}$$

The ratio of the sound pressures $p_{ec}$ and $p_{2\,cc}$ can relatively easily be obtained from measurements of the sound pressure in the ear canal and in the 2 cc coupler. The sound pressure in the 2 cc coupler (for example, for a standard signal) and/or the coupler impedance $Z_{2\,cc}$ can be measured for the individual hearing instrument and stored in its memory. Alternatively, standard values representing an average of the values for a certain hearing instrument model can be stored in the memory.

However, the ear canal parameters/coefficients $e_{12}$ and $e_{22}$ in the above equation need to be estimated. For this, there exist different options.

Figure 5:
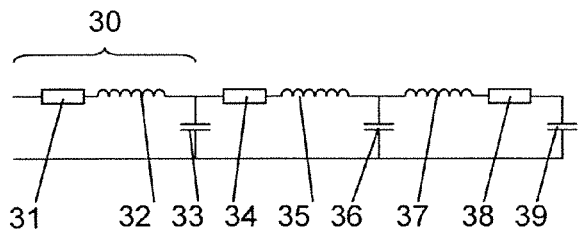
FIG. 5 is a model of the middle and outer ear.

Option 1: Complete model of the outer ear and the middle ear. The network model depicted in FIG. 5 is fitted to the measured ear canal impedance $Z_{ec}$. In the diagram of FIG. 5, the ear is modeled by a circuit of impedances, namely resistors 31, 34, 38, capacitors 33, 36, 39, and inductors 32, 35, 37. In this model, the inductors represent masses, the capacitors the elastic coupling of the masses to each other and to the skull, and the resistors represent acoustic dampers, especially losses in sound transmission. The input-side half T-pad 30 represents the ear canal portion, the transition matrix E of which comprises the parameters $e_{12}$ and $e_{22}$. The fitting is carried out to optimize the values of the masses, capacitors and resistors for the calculated overall impedance as a function of the frequency to the measured input impedance. The transition matrix can then be calculated from the results of the fitting according to the pertinent rules of electrical engineering.

Figure 6:
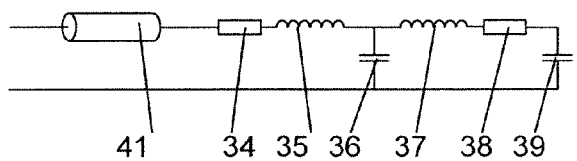
FIG. 6 is another model of the middle and outer ear.
Figure 7A:
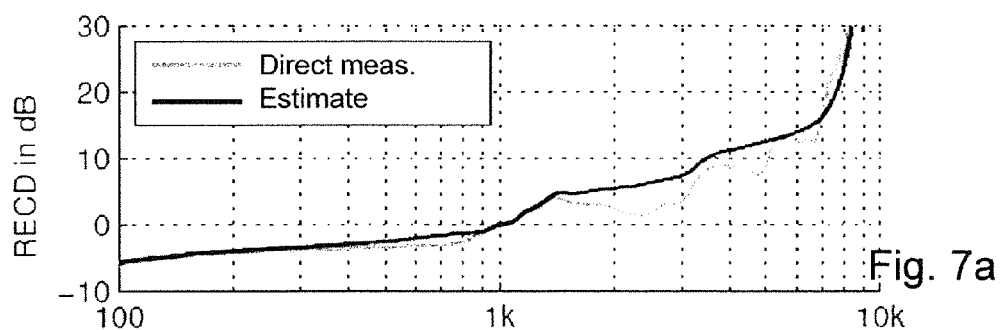
FIGS. 7a-7d are graphs illustrating measured and estimated RECDs for different ears.
Figure 7B:
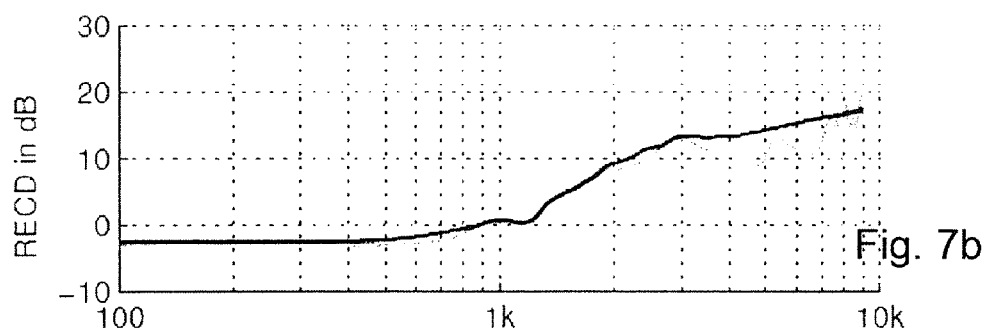
Figure 7C:
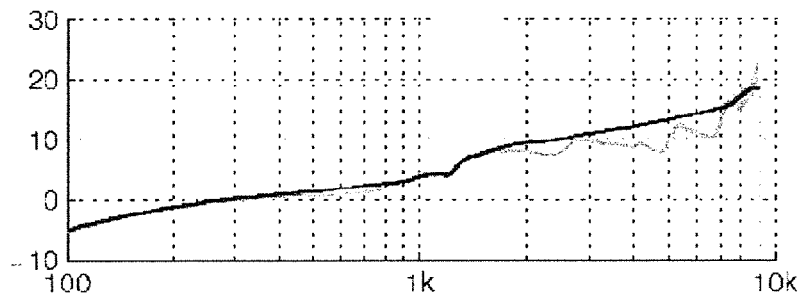
Figure 7D:
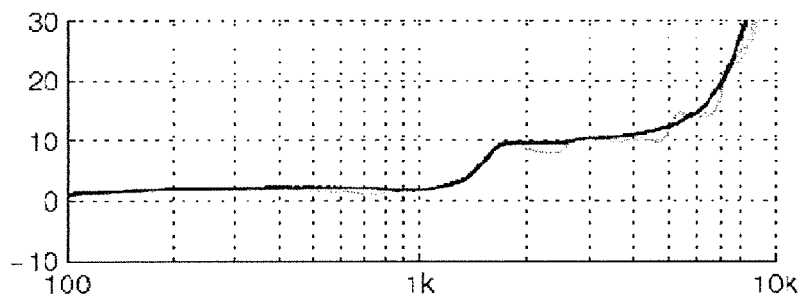

In FIG. 6, the outer ear portion of the model is replaced by a piece of tubing 41. In case of no substantial losses, the properties are described by the two parameters d (diameter, or equivalently A: cross sectional area) and l (length) of the ear canal. The parameters to be determined in this case are:

$$e_{12} = j\frac{\rho c}{A}\sin(kl), \; e_{22} = \cos(kl)$$

For the models of option 1, the input impedance is parametrized, the network elements being the parameters. Thus, also the transfer impedance as well as the eardrum impedance can be described in function of the same parameters.

Option 2: Model of the outer ear with general eardrum impedance. A comparably simple way to estimate the ear canal parameters essentially independently of the knowledge of the eardrum impedance is based on the analysis of the impedance breakdown at the λ/4 resonance of the rest of the ear canal. For approximating the ear canal, the model of the loss-free acoustic conduction is used. The length l of the ear canal element is estimated from the frequency $f_0$ of the λ/4 resonance, which in turn can be determined as a minimum impedance in the impedance measurement in the ear canal. The diameter of the ear canal is not an overly critical value. For the ear canal diameter, for example, in accordance with the ear simulator 711 a value of 7.5 mm is used. An additional consideration of the friction losses is, for example, not made, because the differences for canal elements of this order of magnitude are negligible. From the frequency $f_0$, the length of the canal is given by:

$$l = \frac{c}{4f_0}$$

Given the characteristic impedance $$Z_w = \frac{\rho_0 c}{A}$$

the wanted transition matrix E is:

$$E = \begin{pmatrix} \cos(kl) & jZ_w\sin(kl) \\ j\frac{1}{Z_w}\sin(kl) & \cos(kl) \end{pmatrix}$$

Examples of RECDs estimated by this method and RECDs directly measured are given in FIGS. 7a-7d. The Figures represent directly measured RECD curves (gray lines) and estimates based on a model according to option 2 as a function of frequency in Hz for different ear models, each of FIG.

7a-7d representing a different model. As can be seen, there is a good correspondence between the estimated and the measured RECDs. In the estimates, for the remaining ear canal, a diameter of 7.5 mm was used. The assumed diameter has been found to not be critical.

Figure 8:
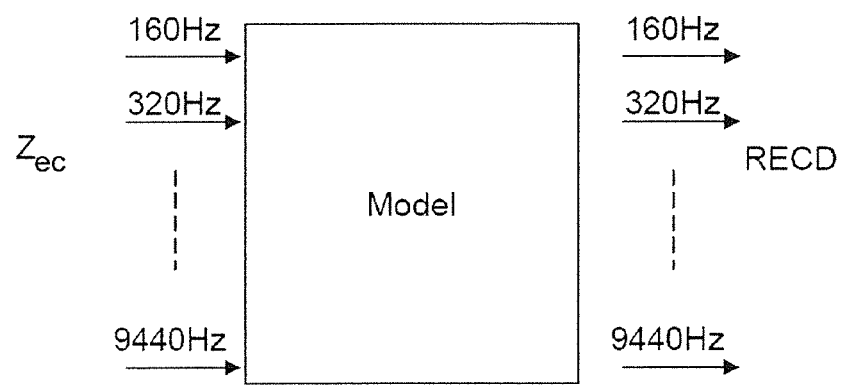
FIG. 8 is a general statistical model.

Option 3: Statistical model. With the help of data from fitted models, the complicated nonlinear relationship between the measured input impedances and the RECD can be interpreted in a comparably easy-to-calculate integral model. FIG. 8 depicts a general scheme of such a model for the direct estimate of the RECD. The frequency dependence in the depicted embodiment is depicted to be represented by the impedance and the RECD given in values in frequency band of a width of 160 Hz, however, other ways to express the frequency dependence—such as frequency bands split differently; possibly unequal splittings between the input impedance frequency bands and the RECD frequency bands, etc.—are of course possible.

The model of FIG. 8 may be set up based on calculations or estimates or phenomenologically or in combinations of these (calculation and estimate, calculation and phenomenology, estimate and phenomenology or all three of them).

Figures 9, 10:
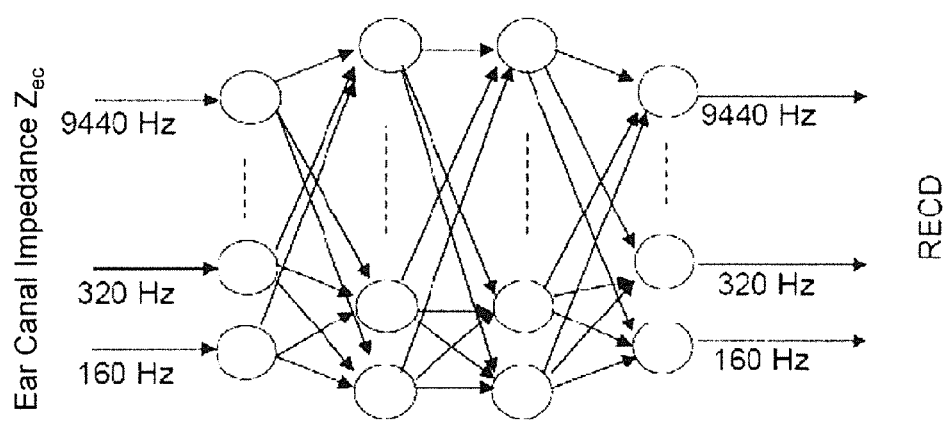
FIG. 9 is a general linear model.
FIG. 10 is a general nonlinear model.

An linear model where the relationship between the ear canal impedance $Z_{ec}$ and the RECD—both represented by a vector the components of which are the according values in the frequency bands—is given by a matrix M is schematically illustrated in FIG. 9.

An example of a nonlinear model is depicted in FIG. 10. In FIG. 10, a non-linear model is given by a neuronal network that can be trained by data obtained by measurement or in an other way.

Further options are feasible.

Figure 13A:
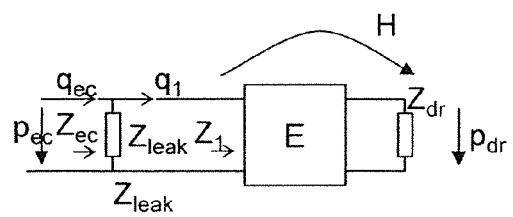
FIGS. 13a and 13b are model that take into account the leak impedance, both, for the transfer from the ear canal to the eardrum with hearing aid excitation (FIG. 13a) and the REOG situation (FIG. 13b) representing the transfer from outside to the eardrum with turned-off hearing instrument.

In FIG. 13a, the transfer function H describes the pressure transfer from the ear canal to the eardrum when the leak—especially by the vent—is not neglected. This transfer function H is independent of the leak impedance $Z_{leak}$, but the ear canal impedance $Z_{ec}$—that that is the measured input impedance—depends on $Z_{leak}$. FIG. 13a depicts a model in which the leak impedance is taken into account. The ear canal impedance $Z_{ec}$ is a function of the leak impedance $Z_{leak}$ and of the input impedance $Z_1$ of the ear canal without leak:

$$Z_{ec} = \frac{p_{ec}}{q_{ec}} = \frac{1}{1/Z_1 + 1/Z_{leak}}$$

Pressure transfer function H and transfer impedance $Z_{trans}$ as functions of the ear canal impedance $Z_{ec}$ are expressed as follows:

$$H = \frac{p_{dr}}{p_{ec}} = e_{22} - \frac{e_{12}}{Z_{ec}} + \frac{e_{12}}{Z_{leak}}$$

$$Z_{trans} = \frac{p_{dr}}{q_{ec}} = e_{22}Z_{ec} - e_{12} + \frac{Z_{ec}}{Z_{leak}}e_{12}$$

For $Z_{leak} \gg Z_{ec}$ (this will generally be justified for vents with a small diameter. Indeed, it has been found that the third term in the last equation containing $Z_{leak}$ in realistic situation lies about 20 dB below the values of the other terms and can thus be neglected) this corresponds to the previously given formula for the transfer impedance.

In addition to the RECD, also the Real Ear Occluded Gain (REOG) is of interest.

Figure 13B:
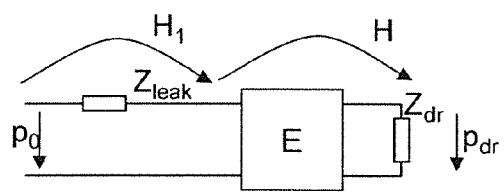

FIG. 13b shows the REOG situation (signal incident only from the outside, through the leaky elements like vent etc.).

In FIGS. 13a and 13b, $Z_{ec}$ and $Z_1$ describe the ear canal input impedance and an impedance of the ear canal without leak, respectively.

In FIG. 13b, the free field sound pressure $p_0$ is transferred through the vent and other leaks with impedance $Z_{leak}$ to the ear canal via the additional transfer function $H_1$, and from there to the eardrum via the transfer function H. Thus, the REOG may be written as $$REOG = \frac{p_{dr}}{p_0} H_1 H$$

From FIG. 13b, it is obvious that $H_1$ is calculated like a voltage divider:

$$H_1 = \frac{Z_1}{Z_1 + Z_{leak}}$$

With the expression for the ear canal impedance:

$$Z_{ec} = \frac{Z_1 Z_{leak}}{Z_1 + Z_{leak}}$$

The desired transfer function is obtained as follows:

$$H_1 = \frac{Z_{ec}}{Z_{leak}}$$

The REOG is a total of both transfer functions $H_1$ and H. With $$H = \frac{p_{dr}}{p_{ec}} = e_{22} - \frac{e_{12}}{Z_{ec}} + \frac{e_{12}}{Z_{leak}}$$

one gets:

$$REOG = \frac{p_{dr}}{p_{ec}} H_1 H = \frac{Z_{ec}}{Z_{leak}} H = \frac{Z_{ec}}{Z_{leak}}\left(e_{22} - \frac{e_{12}}{Z_{ec}} + \frac{e_{12}}{Z_{leak}}\right) = \frac{e_{22}Z_{ec}}{Z_{leak}} - \frac{e_{12}}{Z_{leak}} + \frac{e_{12}Z_{ec}}{Z_{leak}^2}$$

In contrast to the expressions for the RECD, there are no approximations without leak impedance for the REOG. For this reason, $Z_{leak}$ has to be estimated from the ear canal impedance $Z_{ec}$. $Z_{ec}$ is dominated at low frequencies by $Z_{leak}$, and $Z_{leak}$ may be described by a series of L-R. Hence, an approximated leak impedance $Z_{leak\_approx}$ is given by:

$$Z_{lead\_approx} \approx \text{real}\{Z_{ec}(\omega_o)\} + \text{imag}\{Z_{ec}(\omega_0)\}\frac{j\omega}{\omega_0}$$

Figure 14:
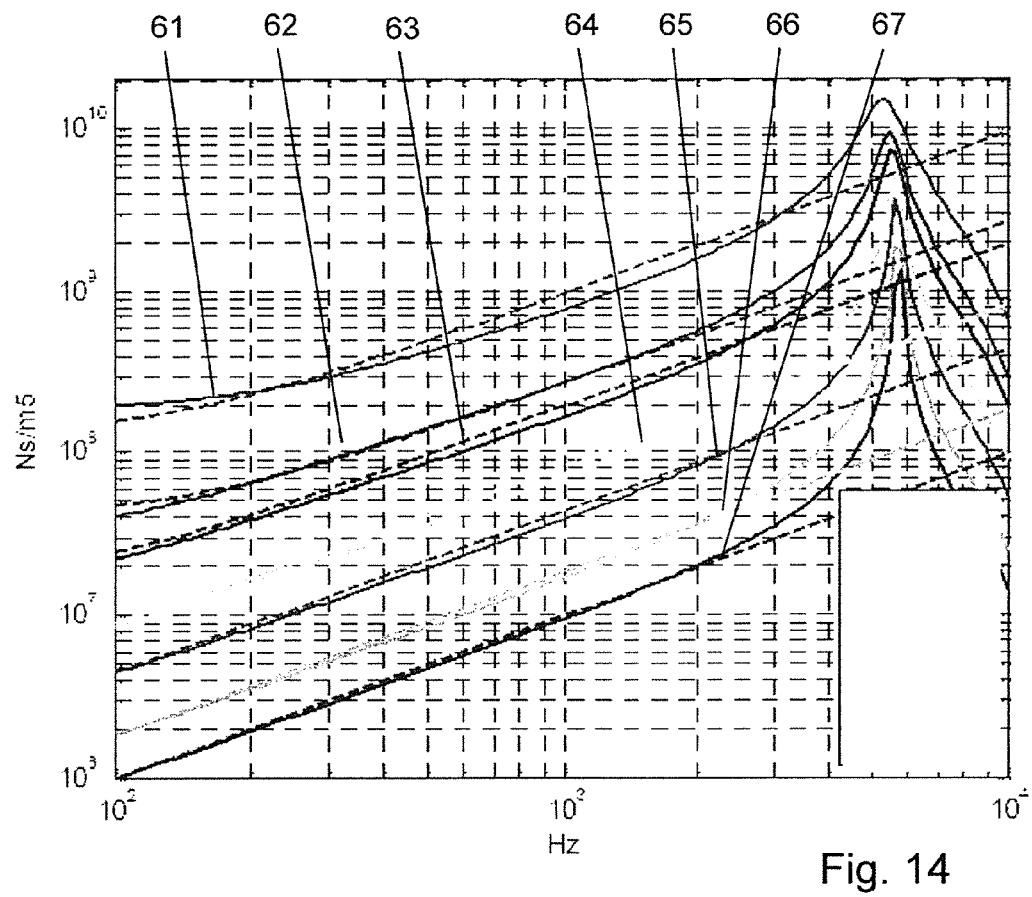
FIG. 14 is a graph illustrating a simulation of the frequency dependence of the leak impedance for different vent diameters and corresponding estimations.

The impedance $Z_{ec}(\omega_0)$ is the impedance at the lowest frequency $f_0 = \omega_0/2\pi$ where reliable measurements are available. FIG. 14 illustrates how this approximation works. The curves represent exact (solid lines) and approximated (dashed lines) solutions for vent diameters of 0.5 mm (61), 0.8 mm (62), 1.0 mm (63), 1.5 mm (64), 2 mm (65), 3 mm (66), and 4 mm (67), respectively. The vent impedances were generated with a Keefe tube model with a length of 15 mm, producing a clearly visible impedance peak at 5.5 kHz. The approximations in each case are within ±2 dB in the range of 0.1-3 kHz, thus the approximation is satisfactory.

With the use of the estimated leak impedance, several approximations for the REOG are possible. Starting from the above equation for the REOG, a first approximation uses only the first term with $e_{22}=1$ (which is a reasonable approximation for low frequencies):

$$REOG \approx \frac{Z_{ec}}{Z_{leak\_approx}}$$

This approximation thus is independent on geometrical properties of the ear canal.

If values different from 1 are taken into account for $e_{22}$ one gets a second approximation:

$$REOG \approx \frac{e_{22} Z_{ec}}{Z_{leak\_approx}}$$

A third approximation takes into account the second term, neglecting the third term $$REOG \approx \frac{e_{22} Z_{ec}}{Z_{leak\_approx}} - \frac{e_{12}}{Z_{leak\_approx}}$$

Figure 15:
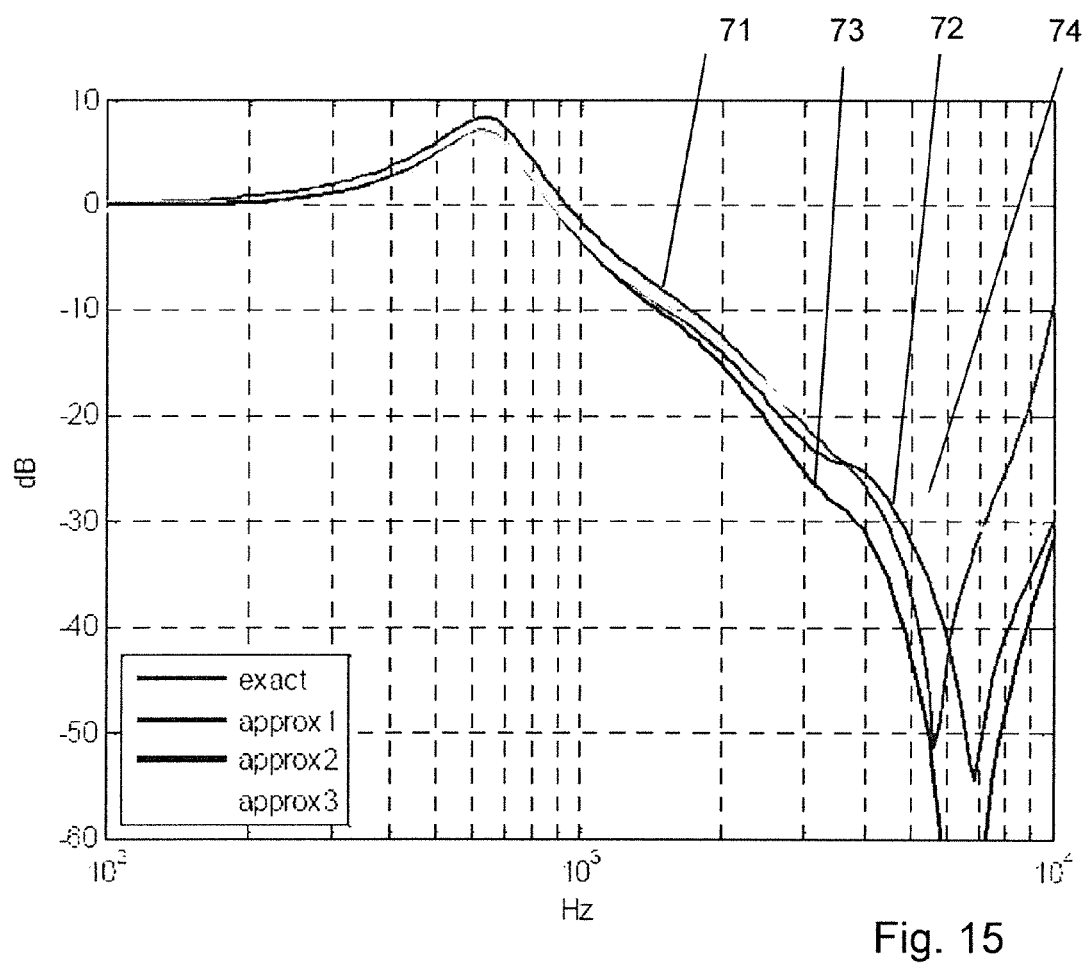
FIG. 15 is a graph illustrating a simulation of the REOG calculated by different approximations.

FIG. 15 shows, for a vent diameter of 2 mm, an exact calculation of the REOG (71), compared to values for the first (72), second (73) and third (74) approximation. Clearly, for frequencies below 3 kHz, all three approximations work well, whereas for high frequencies, due to the uncertainty of the estimation of the leak impedance, more elaborate REOG approximations do not improve the results. Therefore, the first approximation with only one term may be sufficient. It has been found by further measurements, that this first approximation works well over a large range of vent diameters from 0.5-4 mm.

Now, possibilities to obtain the reference characteristics of an acoustic quantity of the hearing instrument coupled to a standard acoustic coupler that is used for determining the acoustic quantity are discussed. These possibilities can be combined with any one of the above options to estimate the physical property of the ear canal. One possibility to obtain the acoustic impedance—especially the input impedance—is to perform a measurement. One advantageous possibility to do so is by way of a calibration element. The calibration element may be shell-shaped with an interior volume of 2 cm² or smaller or larger (note that in the above description, the quantities relating to the calibration element were referred to by the index 2 cc because the RECD as a standard quantity is related to this value. This implies by no means that the calibration volume has to be 2 cm²).

Figure 11:
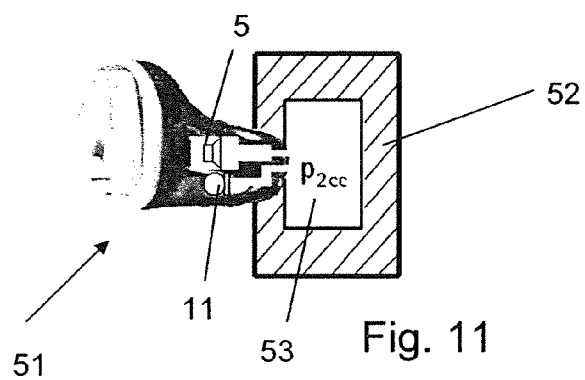
FIGS. 11 and 12 are embodiments of a custom-made calibration element with and without hearing instrument.

An according set-up is depicted in FIG. 11 showing a hearing instrument 51 of the in-the-ear type with the receiver 5 and the ear canal microphone 11 coupled to the test volume 53 of the calibration element 52. One potential disadvantage of such a set-up is potential leakage that especially may distort the low frequency part of the measurement. Therefore, in accordance with the second aspect of the invention, a custom-made calibration element is proposed, the custom-made calibration element being shaped to fit to the also custom-made earpiece of the hearing instrument (the earpiece possibly being the hearing instrument itself if the hearing instrument is of the in-the-ear type.) Especially, the opening of the calibration element may be shaped to have a coupling surface exactly corresponding to a surface portion of the earpiece so that the calibration element's opening fits perfectly to the surface portion even if both, the earpiece and the calibration element are made of materials with little flexibility that do not elastically deform.

Figure 12:
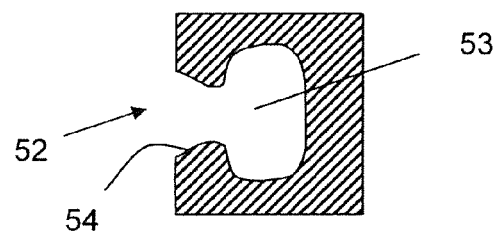

One way to custom-make a calibration element is by methods known from rapid prototyping. For example, there are methods that comprise a layer-by-layer build-up of a three-dimensional object. By such a method, a calibration element shaped the way it is depicted in FIG. 11 is difficult to manufacture. FIG. 12 depicts a calibration element 52 having a shape that is possible to manufacture by such methods. In FIG. 12, reference number 54 denotes the surface portion of the calibration element 52 that is custom-shaped to fit to the according portion of the hearing instrument's earpiece to provide a leakage-free interface.

However, also other methods to manufacture a custom-made calibration element are possible. For example, there exist methods and devices for computer-aided milling of individual shapes. Such methods could be used to make the calibration element 52 starting from a blank with the desired test volume and an opening of reduced shape.

What is claimed is:

1. A method of estimating an acoustic transfer quantity representative of a sound pressure transfer to the eardrum of an ear, when a hearing instrument is coupled to the ear, the method comprising the steps of measuring, by an ear canal microphone of the hearing instrument, an acoustic signal in the ear canal when a sound signal is emitted into the ear canal by a receiver of the hearing instrument, the ear canal microphone being in acoustic communication with the ear canal;

determining, from the acoustic signal and from a frequency dependent ear independent reference characteristics of the hearing instrument, an ear canal impedance; and calculating, from the ear canal impedance, an estimate of the acoustic transfer quantity.

2. The method according to claim 1, wherein the ear independent reference characteristics are reference characteristics of an acoustic quantity of the hearing instrument coupled to a standard acoustic coupler.

3. The method according to claim 1, further comprising, prior to the step of determining the ear canal impedance, the steps of coupling the hearing instrument to a standard acoustic coupler, emitting, by the receiver of the hearing instrument, a sound signal into the standard acoustic coupler, measuring a standard coupler acoustic signal by the ear canal microphone coupled to the standard coupler, and obtaining the reference characteristics from the standard coupler acoustic signal.

4. The method according to claim 3, wherein the standard acoustic coupler is chosen to have a custom manufactured interface with a shape adapted to the shape of a custom manufactured shell of the hearing instrument.

5. The method according to claim 1, comprising, prior to calculating an estimate of the acoustic transfer quantity, at least one of the steps of:

a. estimating a physical property of the ear canal; and b. estimating a leak impedance of sound leaking through a hearing instrument vent and/or through a leaky shell, wherein, in the step of calculating the estimate, the result of estimating the physical property and/or the leak impedance, respectively, is used as a further input quantity in addition to the ear canal impedance.

6. The method according to claim 5, wherein the physical property of the ear canal is chosen to comprise a geometrical quantity characteristic of the ear canal.

7. The method according to claim 6, wherein the physical property is chosen to comprise a distance between a sound emission plane and the eardrum.

8. The method according to claim 7, wherein the step of estimating the distance comprises performing a frequency analysis of the acoustic signal, identifying a frequency at which the signal is at a local extreme and calculating the distance to correspond to a quarter wavelength corresponding to the identified frequency.

9. The method according to claim 1, wherein the transfer quantity is a Real-Ear-to-Coupler difference (RECD) or a Real Ear Occluded Gain (REOG).

10. The method according to claim 1 further comprising the step of adjusting a hearing instrument signal processing parameter dependent on the results of the estimate of the transfer quantity.

11. The method according to claim 1, wherein in the calculation of the ear canal impedance, no measurement data obtained by any separate probe introduced in the ear are used.

12. A hearing instrument comprising at least one input microphone, at least one signal processor, at least one receiver, and at least one ear canal microphone, the receiver and the ear canal microphone being arranged to be in direct communication with a volume defined between an earpiece of the hearing instrument and the eardrum, the signal processor being configured to carry out the method according to claim 1.

13. The hearing instrument according to claim 12, wherein a receiver sound opening at which the signal emitted by the receiver exits into the volume and an ear canal microphone sound opening at which the ear canal microphone or a tubing connected to it connects to the remaining volume define a plane that is approximately perpendicular to an ear canal axis.

* * * * *